United States Patent
Aray

(10) Patent No.: US 8,282,684 B2
(45) Date of Patent: Oct. 9, 2012

(54) INSTANT FACE-LIFTER

(75) Inventor: Ricardo Alfredo Fuenmayor Aray, San Carlos (VE)

(73) Assignee: Ricardo Alfredo Fuenmayor Aray, Brooklyn, NY (US)

( * ) Notice: Subject to any disclaimer, the term of this patent is extended or adjusted under 35 U.S.C. 154(b) by 1135 days.

(21) Appl. No.: 11/893,291

(22) Filed: Aug. 15, 2007

(65) Prior Publication Data

US 2008/0221682 A1    Sep. 11, 2008

(51) Int. Cl.
*A61F 2/02* (2006.01)
(52) U.S. Cl. .................................................. 623/17.18
(58) Field of Classification Search .............. 623/15.11, 623/15.12, 17.18, 8
See application file for complete search history.

(56) References Cited

U.S. PATENT DOCUMENTS

| | | | | | |
|---|---|---|---|---|---|
| 4,574,780 | A | * | 3/1986 | Manders | 128/898 |
| 4,841,992 | A | * | 6/1989 | Sasaki et al. | 128/899 |
| 4,955,395 | A | * | 9/1990 | Manders | 128/898 |
| 5,218,975 | A | * | 6/1993 | Prostkoff | 128/857 |
| 5,876,447 | A | * | 3/1999 | Arnett | 623/17.18 |
| 6,277,150 | B1 | * | 8/2001 | Crawley et al. | 623/17.18 |
| 6,955,690 | B1 | * | 10/2005 | Cao | 623/7 |

* cited by examiner

*Primary Examiner* — Bruce E Snow
*Assistant Examiner* — Melissa Hoban

(57) ABSTRACT

The Instant Face-Lifter is an intra-scalp beautifying device that stretches the face's skin creating a younger appearance with minimum scarring. It consists of an oval-shaped device made of solid medical grade silicone, typically measuring $5^{12}/_{16}$" long×$4^{12}/_{16}$" wide, with sloping edges and an ever increasing thickness in the direction from border to center, starting at a negligible thickness at the borders and increasing to a varying maximum thickness (i.e. ½", ¾", 1", 1 ½", etc.) at its center as to be able to provide the user the desired amount of skin-stretching effect. The upper design of the invention follows a curve which parallels the shape of the skull so that it remains unnoticed from the outside. The invention is slided in the space between the scalp and the galea aponeurotica through a 3" to 4" incision on the parietal area using local anesthesia.

2 Claims, 1 Drawing Sheet

INSTANT FACE-LIFTER

BACKGROUND OF THE INVENTION

The field of endeavor to which the invention pertains, based on the U.S. Patent Classification Definitions, is Class 128, Surgery, subclasses for apparatus which assists a body part or function but does not physically replace or partially replace any normally existing body part, and Sub-Class 899, devices placed entirely within body and means used therewith. This subclass is indented under subclass 897. Subject matter including devices not elsewhere classifiable which are placed entirely within the body either through insertion through natural body openings or by surgical implantation and means used therewith.

Even though there was no prior art to be found in the USPTO literature, this invention is peripherally related to other aesthetic silicone implants, such as breast implants: in both cases, a medical-grade silicone device is permanently implanted under the skin, but being the breast implants filled with liquid silicone, thus increasing its safety concerns due to possible leakaging, whereas the material used in the face-lifter is solid and totally biocompatible medical-grade silicone. Additionally, in this case, the main purpose of the invention is to get an instant face-lifting. The user gets a younger look in minutes, restoring a more youthful, rested, and aesthetic appearance, thus obtaining an approximation of the results obtained through a surgical facelifting but without the high costs involved, the discomfort, or lenghty recovery time, nor the possibility of injury to nerves that control facial muscles, as well as avoiding excess scarring, asymmetry or change in hairline. Neither men would need to shave behind ears, as opposed to cosmetic surgery where beard-growing skin is repositioned.

BRIEF SUMMARY OF THE INVENTION

The Instant Face-Lifter is an intra-scalp beautifying device that helps stretch the face's skin thus instantly improving the face by creating a brighter, softer, fresher appearance with minimum scarring. It consists of an oval-shaped device made of flexible, solid, hypo-allergenic medical grade silicone (or other biocompatible material), typically measuring $5^{12}/_{16}$" long×$4^{12}/_{16}$" wide, with sloping edges and an ever increasing thickness in the direction from border to center, starting at a negligible thickness at the borders and increasing to a varying maximum thickness (i.e. ½", ¾", 1", or 1½") at its center as to be able to provide the user the desired amount of skin stretching effect. The upper part of the invention follows a curve which parallels the shape of the head so the device remains unnoticed from the outside. The invention is slided in the space between the skin of the scalp and the galea aponeurotica of the user through a 3" incision on the parietal (back of the head) area using local anesthesia. Because of the simplicity of its design, the invention provides instant face-lifting thus producing a younger appearing facial structure, elevation of drooping eyebrows, softening of forehead frown lines, and smoothening out vertical lines between the eyebrows, with minimum scarring or possibility of deforming hairline, the implant can be put in place in the convenience of one's home, or at the Doctor's Office; the placement itself is performed without discomfort and under local anesthesia.

BRIEF DESCRIPTION OF THE SEVERAL VIEWS OF THE DRAWING

Listing of figures: (1/1), 3 Figures
FIG. 1. Elevation View

This drawing corresponds to the depiction of the invention as seen from above. The curved lines represent an ever increasing thickness starting from negligible thickness at the borders to a maximum thickness of 1½" at the center of the device. Structural dimensions of the device are indicated as follows: Width (W) and Length (L).

It describes the device as seen sideways, i.e. seen as if it were laying down on a flat surface. Structural dimensions of the device are indicated as follows: Length (L) and Thickness (T).

Figure 1:
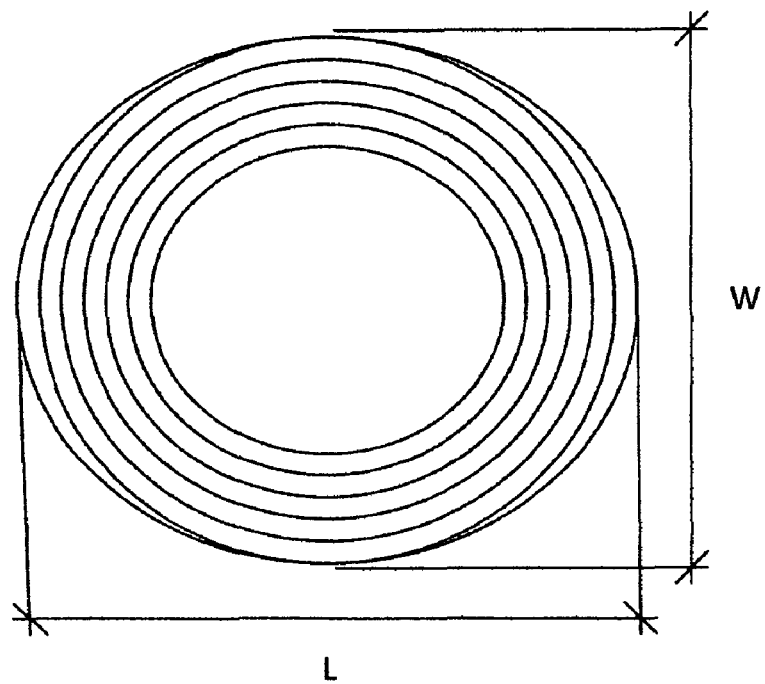
Figure 2:
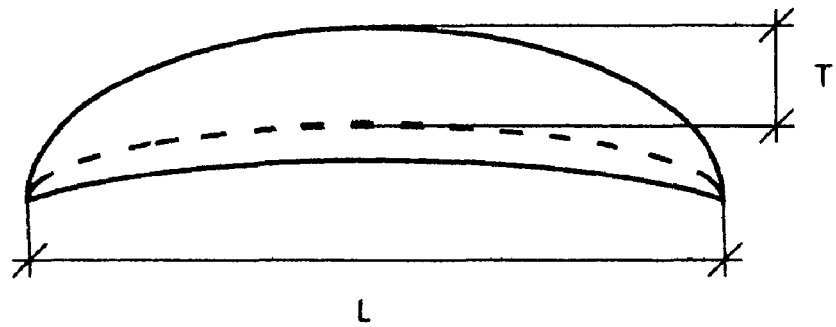
FIG. 2. Plan View
Figure 3:
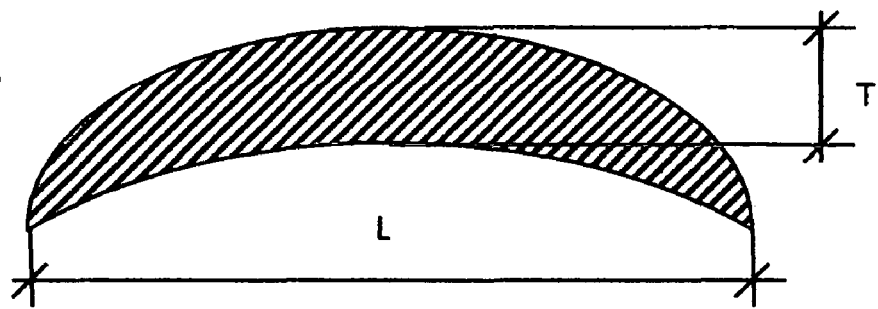

FIG. 3. Section View

It corresponds to a sectional cut through the middle of the device along its longest axis. As it can be seen, it consists basically of 100% solid silicone (or other biocompatible inert material) following the contour of the skull. Its purpose being to stretch the skin of the face, thus smoothening out wrinkles and producing a softer, younger look. Structural dimensions of the device are indicated as follows: Length (L) and Thickness (T).

DETAILED DESCRIPTION OF THE INVENTION

The Instant Face-Lifter, an intra-scalp solid medical-grade silicone (or other biocompatible material) device for instantaneous face lifting, is a beautifying device that helps stretch the face's skin of mid 50's average age users that consists of an elliptical or oval-shaped device made of flexible, solid, hypo-allergenic medical grade silicone (or other biocompatible material), typically measuring $5^{12}/_{16}$" long×$4^{12}/_{16}$" wide, with sloping edges and an ever increasing thickness in the direction from border to center, starting at a negligible thickness at the borders and increasing to a maximum thickness of 1½" at the center. It can be manufactured with varying center's maximum thickness: ½", ¾", 1", 1½", etc., as to be able to provide the user the desired amount of skin stretching effect. In order for the device to be unnoticeable from the outside, the upper part of the invention follows a curve which parallels the shape of the head so there is not a humping effect but rather a natural look. The invention is slided under the scalp, in the space between the skin of the scalp and the superficial musculoaponeurotic system—or galea aponeurotica—, of the user through a 3-in to 4-in incision on the parietal (back of the head) area using local anesthesia, thus instantly improving the face by creating a brighter, softer, fresher appearance with minimum scarring, the user seeing the results in less than half an hour with no down time (as opposed to a lenghty surgical facelifting procedure).

Justification: As we age, our skin naturally begins to lose elasticity and, eventually, may begin to sag and droop. When this condition affects the face, it may cause one to appear older than he or she really is and may even undermine self-confidence. The person may state that others describe him or her as having a tired, worried, or annoyed look. Younger patients may complain that they are misconstrued as aged. Laughing, smiling, crying and squinting are all everyday facial movements that gradually cause one's forehead to develop unwanted furrows, wrinkles and lines. One may have significant crow's feet, deep furrows in one's forehead, jowls or a "second chin" and/or other changes associated with aging: the brows may start their downward descent.

All this usually happens in the third to fourth decades. This, coupled with the inevitable effects of aging, can create forehead and expression lines that lead to a tired, worn look. Thus, the primary goal of the Instant Face-Lifter is to get an instant face-lifting, without all the expense, discomfort and pain brought about by a cosmetic or plastic surgery. With almost no down time, the user gets a younger look in minutes, restoring a more youthful, rested, and aesthetic appearance. The device produces a natural, but younger appearing, facial structure and the elevation of drooping eyebrows without heavy scarring. Ideally, a person's eyebrows should arch on or slightly above the upper orbital rims; the invention lifts heavy eyebrows away from the eyes and smoothes out vertical lines between the eyebrows and transverse lines across the forehead.

(From internet) 9.2 million cosmetic surgery procedures in 2004 in USA

The number of cosmetic plastic surgery procedures increased 5 percent in 2004, compared to 2003, according to statistics by the American Society of Plastic Surgeons (ASPS). Cosmetic procedures are up 24 percent from 2000.

There were 1,421.000 cosmetic surgeries in 2005 in USA. Americans spent just under $12.4 billion on cosmetic procedures; $8.2 billion was for surgical procedures, and $4.2 billion was for nonsurgical procedures Procedure for Implating the Device Under the Scalp The placement itself can be performed without discomfort and under local anesthesia.

1. Start out by injecting the patient's skin with a mixture of lidocaine and adrenaline or a mixture of 1% Xylocaine® and 1:100,000 adrenaline. This is injected along the incision site after appropriate cleaning and draping.

Note1: idocaine® is like Novocain®; it numbs the skin. The adrenaline shrinks the blood vessels so there is little bleeding during the placement of the implant. The hair behind the head is taped up and out of the way. There is no need to shave any of the hair. Put the hair in little pigtails and tie it up with tape to keep it out of our way during the placement of the device.

Note2: When making the incision within the hair, keep the cut parallel to the hair shafts (when the incision of the scalpel parallels the hair shafts, one is able to see the hair follicles like little black bulbs and the shafts of hair arising from the follicles). That way, one is not cutting across the hair shafts close to the skin, or under the skin, and the wounds heal more quickly, and more trouble-free. They also hide better.

2. The skin is incised with a round-tipped knife (number 15). Make a 3 to 4 inch-long horizontal incision on the scalp skin in the parietal area, two inches below the crown of the head in the back of the head. The dissection is made under the superficial temporal fascia.

3. After the incision has been made use a 27-gauge spinal to infiltrate under the scalp to be raised, using the same lidocaine® and epinephrine diluted with normal saline to a 50% concentration, as tumescent solution.

4. The face-lifter is placed in its proper position by pushing its way under, and separating the galea from the scalp in a plane through the loose areolar tissue of the scalp. Thus, the silicone device will work as a separator, lifting the scalp flap from galeal layer up. Basically, one is elevating the skin off of the galea by pushing gently forward the silicone device. The face-lifter will slide over the layer called the aponeurotic system or galea. This region is relatively avascular.

As a second option: It consists of using a sterile 1-ft long soft-tip round-end rigid silicone spatula to gently work your way in under the scalp, using a side-to-side movement, separating the connective tissue that loosely binds the galea to the scalp, thus creating a space for the face-lifter.

5. Suturing: Use 6-0 Prolene® sutures or staples in the hair-bearing region of the parietal region 6. Once the face-lifting device is in place and the incision sutured, the doctor or nurse will place bandages over the incisional areas. Your surgeon will usually recommend removal of the stitches during the first 5 days following the procedure.

7. Because of the excellent blood supply, infection is rare. Appropriate antibiotic coverage is indicated should infection occur. In case there is later clear effusion, it can be cured using aspiration and injection of prednisonein to the capsular.

What is claimed is:

1. An intra-scalp beautifying device for instantaneous face-lifting consisting of a round or elliptically-shaped solid intra-scalp device, possessing a solid body made of solid biocompatible material, measuring $5^{12}/_{16}$ long $\times 4^{12}/_{16}$ wide, having sloping edges and an ever increasing thickness in the direction from border to center, starting at a negligible thickness at the borders and increasing to a varying maximum thickness of $1\frac{1}{2}$ at its center, its upper surface following a curve which parallels the shape of the skull as for it to be unnoticeable from the outside.

2. The device according to claim 1, wherein the solid biocompatible material is either flexible or rigid medical grade silicone or other inert synthetic or naturally derived polymeric material or substance.

\* \* \* \* \*